(12) United States Patent
Yoo et al.

(10) Patent No.: US 11,161,822 B2
(45) Date of Patent: Nov. 2, 2021

(54) AMIDE COMPOUNDS AND USE THEREOF

(71) Applicant: NeoPharm Co., Ltd., Daejeon (KR)

(72) Inventors: Kyung Sook Yoo, Daejeon (KR); Bu-Mahn Park, Daejeon (KR); Min Hee Kim, Bucheon-si (KR); Yu Ra Jung, Daejeon (KR); Hye Seong Shin, Ulsan (KR)

(73) Assignee: NeoPharm Co., Ltd., Daejeon (KR)

( * ) Notice: Subject to any disclaimer, the term of this patent is extended or adjusted under 35 U.S.C. 154(b) by 0 days.

(21) Appl. No.: 16/877,593

(22) Filed: May 19, 2020

(65) Prior Publication Data

US 2020/0392089 A1 Dec. 17, 2020

(30) Foreign Application Priority Data

Jun. 12, 2019 (KR) .......................... 10-2019-0069307

(51) Int. Cl.
*C07D 233/64* (2006.01)
*C07C 235/80* (2006.01)
*C07D 209/20* (2006.01)
*C07C 279/14* (2006.01)

(52) U.S. Cl.
CPC .......... *C07D 233/64* (2013.01); *C07C 235/80* (2013.01); *C07C 279/14* (2013.01); *C07D 209/20* (2013.01)

(58) Field of Classification Search
CPC .. C07D 233/64; C07D 209/20; C07C 235/80; C07C 279/14
USPC ......................................................... 514/400
See application file for complete search history.

(56) References Cited

U.S. PATENT DOCUMENTS 6,518,066 B1 * 2/2003 Oulmassov ............. A61P 31/00
435/468

OTHER PUBLICATIONS

Metzger et al., Mycoloyl peptide and other lipopeptide adjuvants from higher aldoketene dimers, 1987, Angewandte Chemie, 99(4), 343-5 (Year: 1987).*

* cited by examiner

*Primary Examiner* — Kristin A Vajda
(74) *Attorney, Agent, or Firm* — The Webb Law Firm (57) ABSTRACT

Provided are a novel amide compound and a use thereof. According to the present invention, there may be provided a use of a novel amide compound which is harmless to the human body with excellent skin stability and decreases activity of peroxisome proliferator activated receptor gamma (PPAR-γ) to fundamentally inhibit sebum overproduction, thereby providing the skin with an effective effect, and a cosmetic composition including the same.

8 Claims, 2 Drawing Sheets

AMIDE COMPOUNDS AND USE THEREOF

CROSS-REFERENCE TO RELATED APPLICATION

This application claims priority to Korean Patent Application No. 10-2019-0069307 filed Jun. 12, 2019, the disclosure of which is hereby incorporated by reference in its entirety.

TECHNICAL FIELD

The following disclosure relates to a novel amide compound and a use thereof.

BACKGROUND

A sebaceous gland in the skin is a complete secreting gland which secretes a mixture of lipids known as sebum. When sebum is overproduced in a sebaceous gland, dermatological disorders or skin diseases such as acne and seborrheic dermatitis may be caused.

Meanwhile, production of sebum is adjusted by factors influencing proliferation and differentiation of sebaceous gland cells. According to reports, it is known that the production of sebum is adjusted by factors such as male hormones, female hormones, insulin-like growth factors (IGF-1), and peroxisome proliferator activated receptors (PPAR). The sebum produced by sebaceous gland cells is secreted to a skin surface via a hair follicle tube, and it is known that the overproduced sebum changes a structure of lipids between corneocytes on the skin surface to deteriorate a skin barrier function. In addition, when the sebum is overproduced, seborrheic scalpitis bacterium and the like may be overproduced to act as a cause of seborrheic dermatitis, scalpitis, and the like. For this reason, appropriate removal of overproduced sebum and inhibition of overproduced sebum are important for a skin barrier function and maintenance of healthy skin.

For removing the overproduced sebum, hygienic methods such as personal face washing with soap and shampoo use are performed. In addition, as a drug therapy, antifungal agents such as selenium sulfide, azole-based compounds, sodium sulfacetamide, and Terbinafine; and anti-inflammatory agents such as steroids; and the like have been used for patients having skin disorders or skin diseases such as acne and seborrheic dermatitis. However, since the drug components as such are for relieving symptoms of acne, seborrheic dermatitis, and the like, and sebum was not fundamentally inhibited or improved.

Thus, fundamental inhibition or improvement of sebum overproduction may be a method of preventing or treating skin diseases in which sebum overproduction is involved.

SUMMARY

An embodiment of the present invention is directed to providing a novel amide compound.

Another embodiment of the present invention is directed to providing a cosmetic composition including the novel amide compound.

Particularly, an embodiment of the present invention is directed to providing a cosmetic composition which may effectively adjust sebum production by decreasing activity of PPAR-γ which influences maturation of sebaceous gland cells.

Particularly, an embodiment of the present invention is directed to providing a stable cosmetic composition which may be formulated into various formulations without cytotoxicity and skin side effects.

In one general aspect, an amide compound represented by the following Chemical Formula 1, a pharmaceutically acceptable salt thereof, or a solvate thereof, is provided:

[Chemical Formula 1]

wherein $R_1$ and $R_2$ are independently of each other (C1-C30) alkyl;

one selected from $R_3$ and $R_4$ is (C1-C30) alkyl, and the other one is hydrogen or (C1-C30) alkyl;

$R_5$ is hydrogen or (C1-C30)alkyl; and the alkyl of $R_3$ and $R_4$ may be further substituted by one or more substituents selected from hydroxy; (C1-C30) alkoxy; (C1-C30) alkylthio; and amino, guanidino, —(C=O)$NH_2$, —(C=O)OR, (C3-C30) heteroaryl, and salts thereof, in which R is hydrogen or (C1-C30) alkyl, and the heteroaryl contains N.

In the amide compound according to an exemplary embodiment of the present invention, in Chemical Formula 1, $R_3$ may be (C1-C7) alkyl; and $R_4$ may be hydrogen.

In the amide compound according to an exemplary embodiment of the present invention, in Chemical Formula 1, $R_3$ may be (C1-C7) alkyl and the alkyl may be further substituted by one or more substituents selected from hydroxy, (C1-C7) alkoxy, and (C1-C7) alkylthio; and $R_4$ may be hydrogen.

In the amide compound according to an exemplary embodiment of the present invention, in Chemical Formula 1, $R_3$ may be (C1-C7) alkyl and the alkyl may be further substituted by one or more substituents selected from —$NH_2$, guanidino, —(C=O)$NH_2$, (C3-C10) heteroaryl, and salts thereof; and $R_4$ may be hydrogen.

In the amide compound according to an exemplary embodiment of the present invention, in Chemical Formula 1, $R_3$ may be (C2-C7) alkyl and the alkyl may be further substituted by —(C=O)OR, in which R is hydrogen or (C1-C7) alkyl; and $R_4$ may be hydrogen.

The amide compound according to an exemplary embodiment of the present invention may be represented by the following Chemical Formula 2:

[Chemical Formula 2]

wherein $R_1$ and $R_2$ are independently of each other (C1-C30) alkyl; and $R_{11}$ is selected from the following structures, in which $R_{21}$ and $R_{22}$ are independently of each other hydrogen or (C1-C7) alkyl:

In the amide compound according to an exemplary embodiment of the present invention, in Chemical Formula 2, $R_1$ and $R_2$ may be independently of each other (C4-C22) alkyl.

In another general aspect, a cosmetic composition includes an amide compound represented by Chemical Formula 1, a pharmaceutically acceptable salt thereof, or a solvate thereof.

Other features and aspects will be apparent from the following detailed description, the drawings, and the claims.

DETAILED DESCRIPTION OF EMBODIMENTS

The advantages, features and aspects of the present invention will become apparent from the following description of the embodiments with reference to the accompanying drawings, which is set forth hereinafter. The present invention may, however, be embodied in different forms and should not be construed as limited to the embodiments set forth herein. Rather, these embodiments are provided so that this disclosure will be thorough and complete, and will fully convey the scope of the present invention to those skilled in the art. The terminology used herein is for the purpose of describing particular embodiments only and is not intended to be limiting of example embodiments. As used herein, the singular forms "a," "an", and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Hereinafter, the novel amide compound according to the present invention and the use thereof will be described, however, technical terms and scientific terms used herein have the general meaning understood by those skilled in the art to which the present invention pertains unless otherwise defined, and a description for the known function and configuration which may unnecessarily obscure the gist of the present invention will be omitted in the following description.

The term "sebum" in the present specification refers to an oily secretion secreted on a hair surface and a skin epidermal surface from sebaceous glands. When the sebum is excessively secreted, skin diseases such as acne get worse, enlarged pores by acne are promoted, and skin diseases may be caused, like dermatitis occurring. In addition, sebum overproduction in the present specification may refer to sebum which is hypersecreted by sebaceous gland cells, and may be a term having a meaning equivalent to the expressions of sebum hypersecretion and the like.

The term "applying" in the present specification refers to bringing the composition according to the present invention into contact with the skin of an individual by an optional appropriate method, which is intended to absorb the composition into the skin.

The term "improvement" used in the present invention refers to all actions to make a state better, or change a state advantageously by applying the composition according to the present invention.

The terms "alkyl", "alkoxy", and other substituents including an alkyl part in the present specification include both forms of straight chain and branched chain.

The term "amino" in the present specification refers to —$NR_aR_b$, wherein $R_a$ and $R_b$ may be independently of each other hydrogen or (C1-C30) alkyl.

The term "guanidino" in the present specification may refer to

The term "heteroaryl" in the present specification refers to an organic radical derived from an aromatic ring by the removal of hydrogen, and may be an organic radical derived from a monocyclic or polycyclic aromatic ring containing 3 to 8 ring atoms including a nitrogen atom (N) or the like.

The term "pharmaceutically acceptable salt" in the present specification refers to a salt or composite which retains a desired biological activity of the amide compound of the present invention and represents an undesirable toxicity effect at the minimum or no undesirable toxicity effect. Specifically, the pharmaceutically acceptable salt may be an acid addition salt which is formed of an inorganic acid such as hydrochloric acid, hydrobromic acid, sulfuric acid, nitric acid, and phosphoric acid; or an organic acid such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalene sulfonic acid, 4-toluene sulfonic acid, camphorsulfonic acid, 4-methylbicyclo [2.2.2]-oct-2-ene-1-carboxylic acid, glucoheptonic acid, 3-phenylpropionic acid, trimethylacetic acid, tert-butylacetic acid, lauryl sulfuric acid, gluconic acid, glutamic acid, hydroxynaphthoic acid, salicylic acid, stearic acid, and muconic acid.

The term "solvate" in the present specification may refer to a higher-order compound produced between molecules or ions of a solute and molecules or ions of a solvent and ions, and as an example, a hydrate to which water is bonded may be included.

In addition, the singular form used in the present specification may be intended to also include a plural form, unless otherwise indicated in the context.

In addition, units used in the present specification without particular mention is based on weights, and as an example, a unit of % or ratio refers to a wt % or a weight ratio.

In addition, the numerical range used in the present specification includes all values within the range including the lower limit and the upper limit, increments logically derived in a form and span in a defined range, all double limited values, and all possible combinations of the upper limit and the lower limit in the numerical range defined in different forms.

In addition, in the present specification, the expression "comprise" is an open-ended description having a meaning equivalent to the expression such as "is/are provided with", "contain", "have", or "is/are characterized", and does not exclude elements, materials or processes which are not further listed.

The present applicant repeated a study for a component having excellent efficacy/effect in the inhibition of sebum overproduction which may be stably applied to the human body without a side effect, and during the study, devised a novel amide compound, thereby suggesting the present invention.

The amide compound according to the present invention shows an excellent effect in inhibiting and decreasing expression of peroxisome proliferator activated receptor gamma (PPAR-γ). That is, the amide compound according to the present invention effectively inhibits sebum hypersecretion, by inhibiting factors influencing proliferation and differentiation of cells related to sebum production. Furthermore, since the amide compound of the present invention not only has the effect which is remarkable as compared with various compositions derived from conventional natural herb medicines, but also does not cause side effects even when applied to the human body without toxicity to the skin, the compound has excellent utilization as the cosmetic composition.

In particular, since the amide compound according to the present invention effectively inhibits expression of peroxisome proliferator activated receptor gamma, effective effects for not only the skin diseases resulting therefrom but also diseases of various aspects and the like are expected.

Hereinafter, the present invention will be described in detail.

The amide compound according to an exemplary embodiment of the present invention may be represented by the following Chemical Formula 1, and includes a pharmaceutically acceptable salt or a solvate of the amide compound.

[Chemical Formula 1]

wherein $R_1$ and $R_2$ are independently of each other (C1-C30) alkyl;

one selected from $R_3$ and $R_4$ is (C1-C30) alkyl, and the other one is hydrogen or (C1-C30) alkyl;

$R_5$ is hydrogen or (C1-C30)alkyl; and the alkyl of $R_3$ and $R_4$ may be further substituted by one or more substituents selected from hydroxy; (C1-C30) alkoxy; (C1-C30) alkylthio; and amino, guanidino, —(C=O)$NH_2$, —(C=O)OR, (C3-C30) heteroaryl, and salts thereof, in which R is hydrogen or (C1-C30) alkyl, and the heteroaryl contains N or the like.

In the amide compound according to an exemplary embodiment of the present invention, in Chemical Formula 1, $R_3$ may be (C1-C7) alkyl; and $R_4$ may be hydrogen.

As an example, in Chemical Formula 1, $R_3$ may be methyl, ethyl, or n-propyl; and $R_4$ may be hydrogen.

In the amide compound according to an exemplary embodiment of the present invention, in Chemical Formula 1, $R_3$ may be (C1-C7) alkyl and the alkyl may be further substituted by one or more substituents selected from hydroxy, (C1-C7) alkoxy, and (C1-C7) alkylthio; and $R_4$ may be hydrogen.

As an example, in Chemical Formula 1, $R_3$ may be *-$L_1$-$R_c$, in which $L_1$ is (C1-C4) alkylene, and $R_c$ is further substituted by one or more substituents selected from hydroxy, (C1-C4) alkoxy, and (C1-C4) alkylthio; and $R_4$ may be hydrogen.

As an example, in Chemical Formula 1, $R_3$ may be *-$L_1$-$R_c$, in which $L_1$ is (C1-C4) alkylene, and $R_c$ is further substituted by one or more substituents selected from hydroxy, methoxy, ethoxy, methylthio (*—S-Me, Me is methyl), and ethylthio (*—S-Et, Et is ethyl); and $R_4$ may be hydrogen.

In the amide compound according to an exemplary embodiment of the present invention, in Chemical Formula 1, $R_3$ may be (C1-C7) alkyl and the alkyl may be further substituted by one or more substituents selected from —$NH_2$, guanidino, —(C=O)$NH_2$, (C3-C10) heteroaryl, and salts thereof; and $R_4$ may be hydrogen.

As an example, in Chemical Formula 1, R$_3$ may be *-L$_2$-R$_d$, in which L$_2$ is (C1-C4) alkylene, and R$_d$ is further substituted by one or more substituents selected from NH$_2$, guanidino, —(C=O)NH$_2$, indolyl, imidazolyl, and salts thereof; and R$_4$ may be hydrogen.

As an example, the form of the salt may be *—NH$_3^+$ and the like, and the definition of R$_{11}$ in Chemical Formula 2 described later will be referenced.

In the amide compound according to an exemplary embodiment of the present invention, in Chemical Formula 1, R$_3$ may be (C2-C7) alkyl and the alkyl may be further substituted by —(C=O)OR, in which R is hydrogen or (C1-C7) alkyl; and R$_4$ may be hydrogen.

As an example, in Chemical Formula 1, R$_3$ may be *-L$_3$-R$_e$, in which L$_3$ is (C2-C4) alkylene, R$_e$ is —(C=O)OR, and R is hydrogen, methyl, ethyl, or n-propyl; and R$_4$ may be hydrogen.

The amide compound according to an exemplary embodiment of the present invention may be represented by the following Chemical Formula 2:

[Chemical Formula 2]

wherein

R$_1$ and R$_2$ are independently of each other (C1-C30) alkyl; and

R$_{11}$ is selected from the following structures, in which R$_{21}$ and R$_{22}$ are independently of each other hydrogen or (C1-C7) alkyl:

-continued

As an example, in Chemical Formula 2, R$_1$ and R$_2$ may be independently of each other (C4-C30) alkyl.

As an example, in Chemical Formula 2, R$_1$ and R$_2$ may be independently of each other (C4-C25) alkyl.

As an example, in Chemical Formula 2, R$_1$ and R$_2$ may be independently of each other (C4-C20) alkyl.

In addition, the present invention provides a cosmetic composition including an amide compound represented by Chemical Formula 1, a pharmaceutically acceptable salt thereof, or a solvate thereof.

The cosmetic composition according to an exemplary embodiment of the present invention may be a cosmetic composition for inhibiting sebum hypersecretion. Here, the cosmetic composition for inhibiting hypersecretion may be a cosmetic composition for inhibiting and adjusting sebum secretion.

The cosmetic composition for inhibiting sebum hypersecretion according to an exemplary embodiment of the present invention includes the amide compound as an effective component, thereby effectively inhibiting overproduced sebum simultaneously with showing excellence in lipid accumulation inhibition effect in the skin. In particular, the cosmetic composition may effectively inhibit formation of a comedone which is a basic lesion of acne, resulting from vigorous sebum secretion and follicle blockage therefrom, thereby effectively acting on prevention and improvement of skin diseases such as acne.

Thus, the cosmetic composition for inhibiting sebum hypersecretion according to an exemplary embodiment of the present invention may be usefully utilized also as a cosmetic composition having a use of providing an effective effect for prevention and improvement of skin diseases such as acne.

The cosmetic composition for inhibiting sebum hypersecretion according to an exemplary embodiment of the present invention is a very stable material and is easy for formulation development, and in terms of an excellent activity decrease in peroxisome proliferator activated receptor gamma, may include the amide compound having the following structural characteristic.

As an example, in Chemical Formula 1, R$_3$ may be (C1-C7) alkyl; and R$_4$ may be hydrogen.

As an example, in Chemical Formula 1, R$_3$ may be (C1-C7) alkyl and the alkyl may be further substituted by one or more substituents selected from hydroxy, (C1-C7) alkoxy, and (C1-C7) alkylthio; and R₄ may be hydrogen.

As an example, in Chemical Formula 1, R₃ may be (C1-C7) alkyl and the alkyl may be further substituted by one or more substituents selected from —NH₂, guanidino, —(C═O)NH₂, (C3-C10) heteroaryl, and salts thereof; and R₄ may be hydrogen.

As an example, in Chemical Formula 1, R₃ may be (C2-C7) alkyl and the alkyl may be further substituted by —(C═O)OR, in which R is hydrogen or (C1-C7) alkyl; and R₄ may be hydrogen.

More specifically, the cosmetic composition for inhibiting sebum hypersecretion according to an exemplary embodiment of the present invention may include an amide compound represented by the following Chemical Formula 2:

[Chemical Formula 2]

wherein

R₁ and R₂ are independently of each other (C1-C30) alkyl; and

R₁₁ is selected from the following structures, in which R₂₁ and R₂₂ are independently of each other hydrogen or (C1-C7) alkyl:

As an example, in Chemical Formula 2, R₁ and R₂ may be independently of each other (C4-C30) alkyl.

As an example, in Chemical Formula 2, R₁ and R₂ may be independently of each other (C4-C25) alkyl.

As an example, in Chemical Formula 2, R₁ and R₂ may be independently of each other (C4-C20) alkyl.

As an example, in Chemical Formula 2, R₂₁ and R₂₂ may be independently of each other hydrogen, methyl, ethyl, n-propyl, or the like.

In addition, the cosmetic composition for inhibiting sebum secretion according to an exemplary embodiment of the present invention includes the compound represented by Chemical Formula as an effective component, thereby being formulated into various forms of cosmetic composition. In addition, the use amount of the effective component may be appropriately adjusted depending on not only implementation of an activity decrease effect of peroxisome proliferator activated receptor gamma to be desired but also requirements such as skin safety, ease during formulation, and the like, of course.

The cosmetic composition for inhibiting sebum secretion according to an exemplary embodiment of the present invention may include the effective component at 0.001 to 50 wt %, based on the total weight of the cosmetic composition. The effective component may be included at specifically 0.01 to 30 wt %, and more specifically 0.01 to 20 wt %.

As an example, the effective component may be included at 0.01 to 10 wt %.

As an example, the effective component may be included at 0.01 to 5 wt %.

As an example, the effective component may be included at 0.01 to 3 wt %.

In addition, the cosmetic composition for inhibiting sebum secretion according to an exemplary embodiment of the present invention is combined with a solid powder to impart surprisingly remarkable synergy in not only sebum secretion inhibition but also hypersecreted sebum inhibition.

The solid powder may be selected from inorganic particles, organic particles, organic and inorganic composite particles, and the like. In addition, the solid powder may be in the form of a sphere, a plate, and the like.

The solid powder in the form of a sphere may be silica, polymethylmethacrylate, an ethylene/acrylic acid copolymer, and the like.

As an example, the solid powder in the form of a sphere may have an average particle diameter of less than 5 μm.

The solid powder in the form of a plate may be talc, mica, boron nitride, barium sulfate, alumina, sericite, kaolin, and synthetic fluorophlogopite, and the like.

As an example, the solid powder in the form of a plate may have an average thickness of 0.1 to 1.0 μm and an average particle diameter of 1 to 100 μm.

As an example, the solid powder in the form of a plate may have an aspect ratio of 10 or more. The aspect ratio means a thickness degree of a cross section perpendicular to a widest cross section of the solid powder in the form of a plate, and may mean the shortest diameter ratio.

In addition, the solid powder may be included at 0.01 to 5 wt % based on the total weight of the cosmetic composition. The solid powder may be included at specifically 0.05 to 3 wt %, and more specifically 0.1 to 2 wt %.

Hereinafter, the specific use of the present invention will be described.

The use of the present invention may be an activator inhibitor of peroxisome proliferator activated receptor gamma including the amide compound described above as an effective component.

The activator inhibitor of peroxisome proliferator activated receptor gamma according to an exemplary embodiment of the present invention decreases activity of PPAR-γ to effectively inhibit sebum production, and thus, may be utilized in an in-vitro or in-vivo test, or the like, utilizing the use.

As an embodiment, the activator inhibitor of peroxisome proliferator activated receptor gamma may be utilized for confirming the effect of inhibiting hypersecreted sebum. That is, the activator inhibitor of peroxisome proliferator activated receptor gamma may be utilized as an evaluation indicator for confirming the effect of inhibiting hypersecreted sebum.

As an embodiment, the activator inhibitor of peroxisome proliferator activated receptor gamma may be utilized as an indicator for measuring the effect of prevention and improvement of skin diseases according to effective inhibition of hypersecreted sebum. Here, an example of the skin disease may be acne, seborrheic dermatitis, and the like, but is not limited thereto.

In addition, the use of the present invention may be a cosmetic composition for inhibiting sebum hypersecretion.

Specifically, the use of the present invention may be a cosmetic composition for adjusting sebum secretion by decreasing activity of peroxisome proliferator activated receptor gamma and inhibiting hypersecreted sebum.

As an embodiment, the cosmetic composition may be for prevention and improvement of skin diseases such as acne and seborrheic dermatitis.

As an embodiment, the cosmetic composition may be for inhibiting formation of a comedone which is a basic lesion of acne.

Since the cosmetic composition for inhibiting sebum hypersecretion according to an exemplary embodiment of the present invention includes the amide compound according to the present invention, it shows excellence in the effect of inhibiting sebum secretion. Moreover, when the cosmetic composition is combined with a solid powder and applied to a formulation, it is noticeable that a surprisingly remarkable effect on sebum inhibition is shown.

The cosmetic composition according to an exemplary embodiment of the present invention may be mixed with purified water, oil, and the like, excluding the amide compound, the solid powder, and the like according to the present invention, and formulated into formulations of various embodiments.

The oil is used without limitation as long as it is commonly used, of course. A non-limiting example thereof may include one or a mixture of two or more selected from a hydrocarbon-based oil, a higher fatty alcohol-based oil, a glyceride-based oil, a silicone-based oil, an ester-based oil, a vegetable oil, an animal oil, a fluorine-based oil, and the like.

In addition, the cosmetic composition according to an exemplary embodiment of the present invention may further include an appropriate additive which is commonly used and be formulated. Here, a non-limiting example of the additive may include one or more selected from one or more aqueous additives selected from a stabilizer, an emulsifier, a thickening agent, a moisturizer, a liquid crystal film enhancer, a pH controlling agent, an antimicrobial, an aqueous polymer, a coating agent, a metal ion sequestering agent, an amino acid, an organic amine, a polymer emulsion, a pH adjusting agent, a skin nutrient, an anti-oxidant, an anti-oxidant auxiliary agent, a preservative, flavoring, and the like; and one or more oily additives selected from fat and oils, waxes, higher fatty acids, and higher alcohols.

Here, the aqueous additive is not limited, as long as it is commonly used in the art, and a non-limiting example thereof may include one or more selected from glycerin, dipropylene glycol, butylene glycol, pentylene glycol, methyl propanediol, sorbitol, diglycerin, erythritol, pentaerythritol, polybutyleneglycol-10, polyglycerin-3, polyglycerin-4, polyglycerin-6, polyglycerin-10, polyglycerin-20, polyglycerin-40, sorbeth-5, sorbeth-6, sorbeth-20, sorbeth-30, sorbeth-40, inositol, maltitol, maltose, mannan, mannitol, mannose, lactitol, lactose, dihydroxypropyl PG-glucoside, dithiaoctanediol, fructose, glucamine, methyl glucamine, glucose, 1,2,6-hexanethiol, methyl gluceth-10, methyl gluceth-20, ozonized glycerin, phytantriol, thiglycerin, threitol, trimethylolpropane, xylitol, EDTA, guar gum, quince seeds, carrageenan, galactan, arabic gum, pectin, mannan, starch, xanthan gum, curdlan, methyl cellulose, hydroxy ethyl cellulose, carboxymethyl cellulose, methyl hydroxypropyl cellulose, chondroitin sulfuric acid, dermatan sulfuric acid, glycogen, heparan sulfuric acid, hyaluronic acid, sodium hyaluronate, tragacanth gum, keratan sulfuric acid, chondroitin, mucoitin sulfuric acid, hydroxyethyl guar gum, carboxymethyl guar gum, dextran, kerat sulfuric acid, locust bean gum, succinoglucan, caronic acid, chitin, chitosan, carboxymethyl chitin, agar, polyvinyl alcohol, polyvinyl pyrrolidone, carboxyvinyl polymer, sodium polyacrylate, polyethylene glycol, bentonite, methylparaben, propylparaben, phenoxyethanol, 1,2-hexanediol, ethylhexyl glycerin, and the like. In addition, the oily additive is not limited as long as it is a raw material commonly used in the art, and a non-limiting example thereof may include liquid oils such as triglyceride, glycerin trioctanoate, and glycerin triisopalmitate, solid oils such as palm oil, hydrogenated palm oil, palm oil, hydrogenated oil, and hydrogenated castor oil, beeswax, candelilla wax, carnauba wax, lanolin, jojoba wax, and the like. An example of the higher fatty acid may include waxes such as lauric acid, myristic acid, palmitic acid, stearic acid, and behenic acid, higher alcohols such as cetyl alcohol, stearyl alcohol, behenyl alcohol, myristyl alcohol, and cetostearyl alcohol, and the like.

Here, the additive may be included at 0.01 to 20 wt %, specifically 0.01 to 10 wt %, or 0.05 to 10 wt %, based on the total weight of the cosmetic composition, but is not limited thereto.

In addition, the cosmetic composition according to an exemplary embodiment of the present invention may be formulated into a formulation selected from the group consisting of an emollient, an astringent, a nutritional toner, an eye cream, a nourishing cream, a massage cream, a cleansing cream, a cleansing foam, a cleansing water, a powder, an essence, a face pack, and the like.

Hereinafter, preferred examples will be provided in order to assist understanding of the present invention. However, the following examples are only provided for easily understanding of the present invention and are only illustrative, and do not limit the scope of the present invention in any way.

(Evaluation Method)

1. Effect of Inhibiting Expression of PPAR-γ by Western Blot

In the present invention, $1.5\times10^5$ (1 mL/well) of human sebocytes were adhered on a 12-well plate containing a Dulbecco's modified eagle medium (DMEM)/F12 (1:1) containing 10% fetal bovine serum (FBS). After culturing for 24 hours, cells were collected after 24 hours from each sample of a control group (1 μM) in which the medium was replaced with a serum-free medium and previously treated with IGF-1 (50 ng/ml) and an experimental group in which the control group was treated with Compound 1 of Example 1 (20 μM). In addition, in the present invention, the control means a sample which was not treated with IGF-1, and the comparative group means a sample in which the control group was treated with retinoic acid (20 μM). Thereafter, expression of PPAR-γ protein which is a representative lipid synthetic transcription factor of sebocytes was analyzed by the Western blot, for each of these samples.

Figure 1:
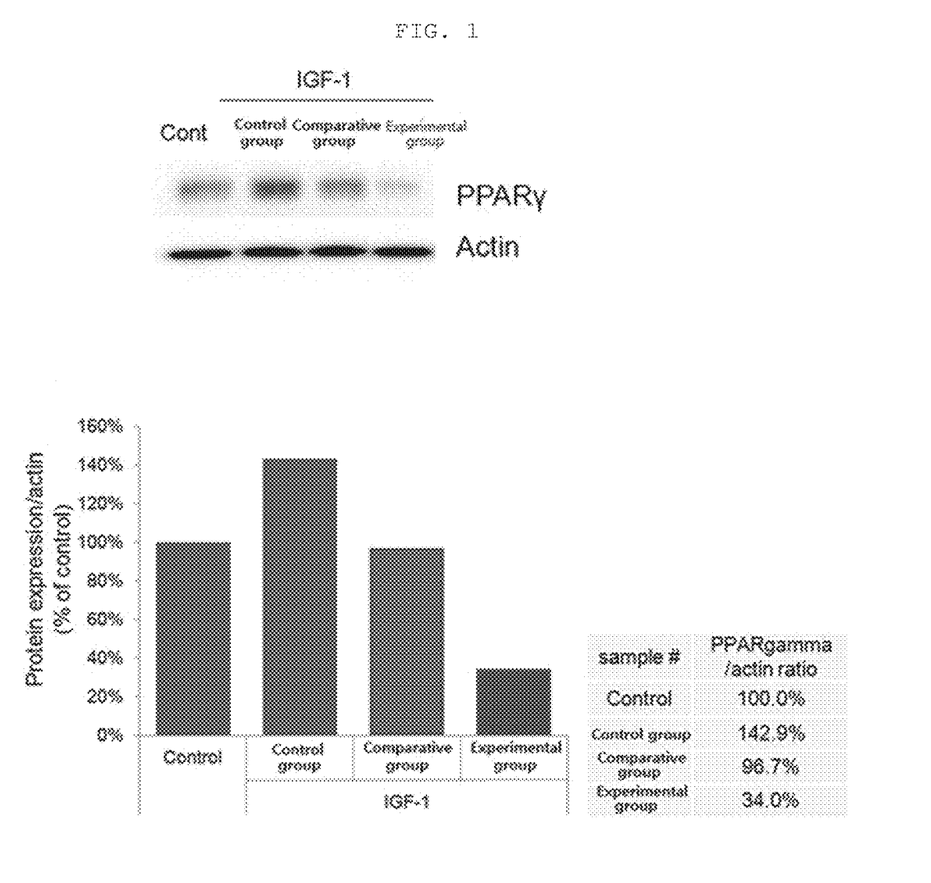
FIG. 1 shows results of expression inhibition of PPAR-γ which is a main lipid synthesis transcription factor in sebaceous gland cells.

The results are shown in the following FIG. 1.

2. Effect of Inhibiting Sebum Secretion $1\times10^5$ (1 mL/well) of human sebocytes were adhered on a 12-well plate containing a Dulbecco's modified eagle medium (DMEM)/F12 (1:1) containing 10% fetal bovine serum (FBS).

Figure 2:
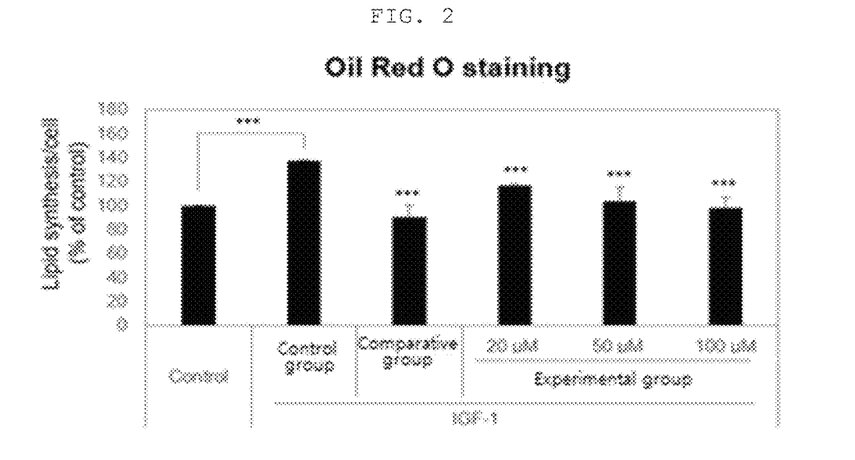
FIG. 2 shows an effect of lipid synthesis inhibition for each concentration in human sebaceous gland cells by oil red o staining.

In FIG. 2, each sample of a control group (1 μM) which was previously treated with IGF-1 (50 ng/ml) after culturing for 24 hours and an experimental group in which the control group was treated with Compound 1 of Example 1 (20 μM) was stained after 24 hours with a 0.5% oil red 0 solution for 1 hour and treated with 100% isopropanol, and an absorbance was measured by a 500 nm ELISA reader.

Figure 3:
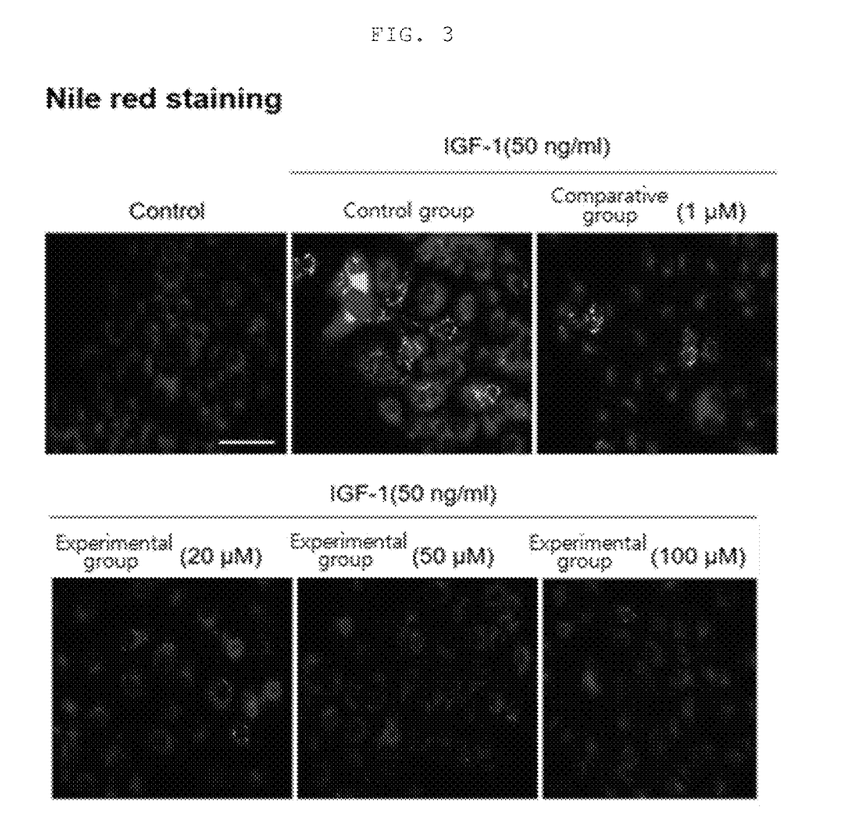
FIG. 3 shows an effect of lipid synthesis inhibition for each concentration in human sebaceous gland cells by nile red staining.

In FIG. 3, after cells were stained with a Nile red (1 ug/ml) solution for 30 minutes, a slide on which one drop of a mounting solution was dropped was covered with a slide cover to which the stained cells were adhered, and after the slide was hardened completely, the slide was observed with a microscopic image.

The results are shown in the following FIG. 2 and FIG. 3.

Example 1

Preparation of Compound 1 (S8-002)

Octanoyl chloride

Octylketendimer

S8-002

Step 1) Preparation of 4-heptylidene-3-hexyloxetan-2-one (octylketendimer)

90 ml of ethyl acetate was added to a 250 ml reactor under a nitrogen atmosphere, and 13 ml (92.89 mol) of triethyl amine (TEA) was added thereto. The temperature of the reactor was cooled to 0° C. or lower using an ice bath, and 15 g (92.22 mmol) of octanoyl chloride was slowly added dropwise. After completing the dropwise addition, the ice bath was removed, the temperature of the reactor was slowly raised to room temperature, and the reactor was stirred for 12 hours. Purified water was added to the reactant, c-HCl was added to lower the pH to 3, the purified water was further added, and the reactant was stirred. Thereafter, the reactant was allowed to stand and an organic layer was separated therefrom. The organic layer was washed with brine once again, and dried with $MgSO_4$. The filtrate was concentrated under reduced pressure to obtain 4-heptylidene-3-hexyloxetan-2-one (octylketendimer) which is a light yellow liquid.

Thereafter, the product was used in the next step without further purification.

Step 2) Preparation of Compound 1 (S8-002)

30 ml of methanol was added to a 250 ml reactor, 6.4 g (46.11 mmol) of alanine methyl ester hydrochloride was added, and 5.1 g (50.72 mmol) of TEA was added. After the reactant was stirred for 10 minutes, 11.6 g (46.11 mmol) of 4-heptylidene-3-hexyloxetan-2-one was slowly added and stirred for 12 hours. The reaction was confirmed with TLC, and the solvent was removed by concentration under reduced pressure. Ethyl acetate and purified water were added to the concentrate. Thereafter, c-HCl was added to adjust pH to 3, and the reactant was stirred and allowed to stand to separate an organic layer. The organic layer was dried with $MgSO_4$, and the filtered filtrate was concentrated under reduced pressure to completely remove the solvent.

Thereafter, the residue was separated with column chromatography (dichloromethane:methanol=50:1) to obtain Compound 1 (S8-002) which was a white solid as a title compound (6.2 g, 17.44 mmol, 38% yield).

MS (ESI pos. ion) m/z: 356 (MH+). Calc'd exact mass for $C_{20}H_{37}NO_4$: 355. $^1H$ NMR (600 MHz, $CDCl_3$): 6.73 (dd, J=42.6, 7.2 Hz, 1H), 4.56-4.52 (m, 1H), 3.74 (d, J=3.0 Hz, 3H), 3.41-3.36 (m, 1H), 2.58-2.49 (m, 2H), 1.85-1.79 (m, 2H), 1.57-1.54 (m, 2H), 1.40 (t, J=7.2 Hz, 3H), 1.32-1.24 (m, 16H), 0.89-0.85 (m, 6H).

As shown in the following FIG. 1, it was confirmed that PPAR-γ was activated by IGF-1 treatment, and activation of PPAR-γ was rather inhibited by retinoic acid treatment which was a positive control group (comparative group). Furthermore, it was confirmed that the effect of inhibiting PPAR-γ activity is remarkable by the treatment with Compound 1 according to the present invention. Thus, it was confirmed that Compound 1 according to the present invention is excellent in effect of inhibiting PPAR-γ activity.

As shown in the following FIG. 2, it was confirmed that according to the control group, the fat content in sebocytes was increased by IGF-1 treatment. However, it was confirmed that a sebum production amount was remarkably decreased by the treatment with Compound 1 according to the present invention. In addition, the effect was significantly increased depending on the treatment concentration of Compound 1 according to the present invention.

In addition, as shown in the following FIG. 3, it was confirmed that differentiation of fat cells is more effectively derived by the treatment with Compound 1 according to the present invention.

From these results, it is confirmed that the effect of inhibiting sebum hypersecretion according to the present invention is achieved by activity inhibition of PPAR-γ which is a transcription regulatory factor related to sebum production and effective fat cell differentiation.

According to the present invention, there may be provided a novel amide compound which has no cytotoxicity and no side effect to the skin, so as to be safely applied to a cosmetic composition of various formulations.

Specifically, the amide compound according to the present invention exerts a useful effect as a cosmetic composition for inhibiting sebum hypersecretion which may decrease the activity of peroxisome proliferator activated receptor gamma (PPAR-γ) to effectively adjust sebum production.

According to the present invention, there may be provided a cosmetic composition which may effectively inhibit hypersecreted sebum simultaneously with appropriately adjusting sebum production. Thus, the cosmetic composition assists not only improvement of skin diseases due to hypersecreted sebum but also maintenance of the characteristic function of healthy skin.

The present invention has been described in detail in specific parts, and it is apparent that such specific technique is only an embodiment to a person skilled in the art, without limiting the scope of the present invention thereto. Thus, the substantial scope of the present invention will be defined by the appended claims and their equivalents.

What is claimed is:

1. An amide compound represented by the following Chemical Formula 1, a pharmaceutically acceptable salt thereof, or a solvate thereof:

[Chemical Formula 1]

wherein
$R_1$ and $R_2$ are independently of each other (C1-C6) alkyl;
one selected from $R_3$ and $R_4$ is (C1-C30) alkyl, and the other one is hydrogen;
$R_5$ is hydrogen or (C1-C30)alkyl; and
the alkyl of $R_3$ or $R_4$ may be further substituted by one or more substituents selected from (C1-C30) alkylthio; and amino, guanidino, —(C=O)NH$_2$, —(C=O)OR, (C3-C30) heteroaryl, and salts thereof, in which R is hydrogen or (C1-C30) alkyl, and the heteroaryl contains N.

2. The amide compound, the pharmaceutically acceptable salt thereof, or the solvate thereof of claim 1, wherein
$R_3$ is (C1-C7) alkyl; and
$R_4$ is hydrogen.

3. The amide compound, the pharmaceutically acceptable salt thereof, or the solvate thereof of claim 1, wherein
$R_3$ is (C1-C7) alkyl and the alkyl is further substituted by one or more substituents selected from (C1-C7) alkylthio; and
$R_4$ is hydrogen.

4. The amide compound, the pharmaceutically acceptable salt thereof, or the solvate thereof of claim 1, wherein
$R_3$ is (C1-C7) alkyl and the alkyl is further substituted by one or more substituents selected from amino (—NH$_2$), guanidino, —(C=O)NH$_2$, (C3-C10) heteroaryl, and salts thereof; and
$R_4$ is hydrogen.

5. The amide compound, the pharmaceutically acceptable salt thereof, or the solvate thereof of claim 1, wherein
$R_3$ is (C2-C7) alkyl and the alkyl is further substituted by —(C=O)OR, in which R is hydrogen or (C1-C7) alkyl; and
$R_4$ is hydrogen.

6. The amide compound, the pharmaceutically acceptable salt thereof, or the solvate thereof of claim 1, wherein the amide compound is represented by the following Chemical Formula 2:

[Chemical Formula 2]

wherein
$R_1$ and $R_2$ are independently of each other (C1-C6) alkyl; and
$R_{11}$ is selected from the following structures, in which $R_{21}$ and $R_{22}$ are independently of each other hydrogen or (C1-C7) alkyl:

-continued

7. The amide compound, the pharmaceutically acceptable salt thereof, or the solvate thereof of claim 1, wherein $R_1$ and $R_2$ are independently of each other (C4-C6) alkyl.

8. A method for decreasing activity of PPAR-γ by applying a compound represented by Chemical Formula 1 as an effective component on skin:

[Chemical Formula 1]

wherein
$R_1$ and $R_2$ are independently of each other (C1-C30) alkyl;
one selected from $R_3$ and $R_4$ is (C1-C30) alkyl, and the other one is hydrogen or (C1-C30) alkyl;
$R_5$ is hydrogen or (C1-C30)alkyl; and
the alkyl of $R_3$ and $R_4$ may be further substituted by one or more substituents selected from hydroxy; (C1-C30) alkoxy; (C1-C30) alkylthio; and amino, guanidino, —(C=O)NH$_2$, —(C=O)OR, (C3-C30) heteroaryl, and salts thereof, in which R is hydrogen or (C1-C30) alkyl, and the heteroaryl contains N.

* * * * *